Dec. 3, 1935. R. L. BYRUM Plant Pat. 156
ROSE
Filed Jan. 9, 1935
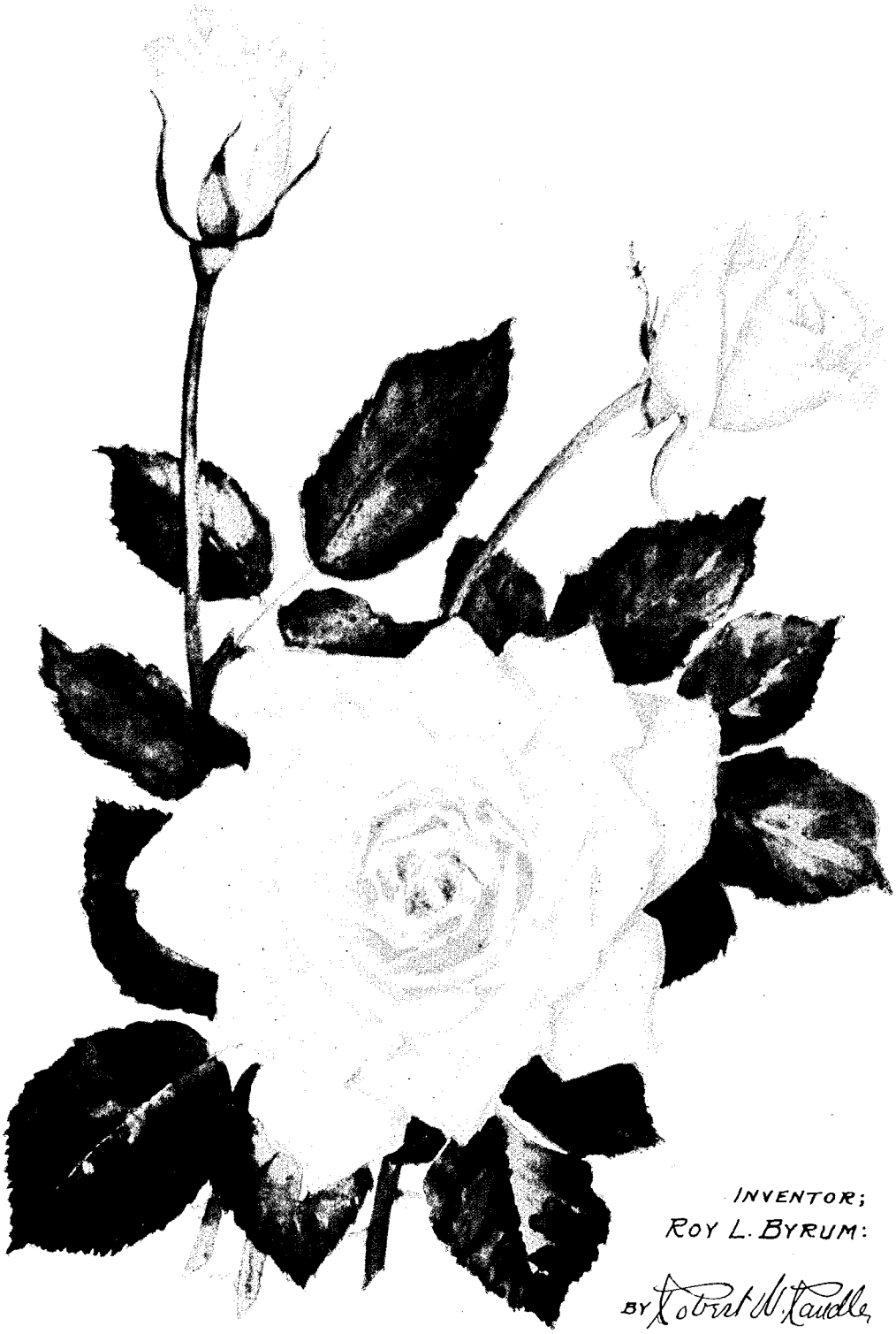
INVENTOR;
ROY L. BYRUM:
BY Robert W. Caudle,
ATTORNEY.

Patented Dec. 3, 1935

Plant Pat. 156

UNITED STATES PATENT OFFICE

156

ROSE

Roy L. Byrum, Richmond, Ind., assignor to Joseph H. Hill Company, Richmond, Ind., a corporation of Indiana Application January 9, 1935, Serial No. 1,043

1 Claim. (Cl. 47—61)

The subject of this application for plant patent is classed as a hybrid tea-rose. It is a seedling of "Sweet Adeline" roses (Rose Patent No. 6) crossed with "Joanna Hill" roses (registered but not patented).

*Generation and propagation.*—I produced this new rose by cutting and budding, after sexual hybridization, employing a Sweet Adeline rose as the male parent, and a Johanna Hill rose as the female parent. The combination of the said two varieties of roses was accomplished as follows:

In the month of March of the year 1930 I collected pollen from the stamens of the male parent and deposited it on the stigmas to conducted it into the ovaries of the female parent. From the product of the above I obtained roses of three distinct new varieties, each of which presented certain new and distinct features, one of said new varieties is the subject of this application, the same being shown, as nearly as was possible, in the accompanying illustration in three stages of development.

The rose which is the subject of this application was reproduced by cutting and grafting and close personal supervision, whereby the features, herein shown and described, have become fixed as a new variety of roses, which features I will now set forth as fully and as clearly as I may. The following description was made from roses grown in the greenhouses of the Joseph H. Hill Company, in Richmond, Indiana, in December 1934.

*Buds.*—The color of the buds before the calyx opens is slightly darker but similar to that of "antimony yellow", shown on Plate XV of Ridgway color chart. As the bud first opens it is substantially identical with said "antimony yellow". As the bud further opens it becomes constantly lighter until the flower is fully open, after which there is no apparent change in the color. Peduncles are long, straight, erect, strong, and rough.

*Bloom.*—The bloom of this rose is considered as perfect. Its form is and remains substantially globular.

The color of the bloom of this particular rose, when viewed at a distance therefrom, appears as an entity, presenting a light "amber" yellowish color, as shown on Plate XVI of Ridgway color chart; but when viewed closely it will be found to consist of various colors and shades, presenting, at least, a three-tone effect, as for instance: The outer portion of the petals are very light with a yellowish tinge, somewhat like the "light-buff", shown on Plate XV of Ridgway color chart, shading gradually into a creamy yellow with a darker color, somewhat darker than said "antimony yellow", at the inner portion of the flower. Reflected blending of colors and shades sometimes cause reddish appearance of parts of the petals.

The texture of the petals is especially fine, waxy and attractive, and they are not easily bruised, and hold their colors for a long period of time. There is no especial difference between the color of the upper and the under sides of the petals.

When fully opened the bloom is classed as double, at which time the bloom is usually five inches in diameter.

*Genitals.*—The stamens are of a "scarlet" color, as on Plate I, of Ridgway color chart, and the anthers are an "apricot yellow", similar to that shown on Plate IV of Ridgway color chart, and they are very prominent. The pollen is a dark yellow color, similar to "Cadman yellow", shown on Plate III of Ridgway color chart. Stigmas are of light glossy yellowish color.

*Foliage.*—The upper surface of the leaves are dark green and their under faces are a pale green, with the new growth much lighter. The foliage is heavy and it is composed of compound leaves of usually three leaflets nearest the flowers and five to seven leaves further down on the stems.

*Bush.*—The bush, as an entirety, is of quick and vigorous growth, with many branches, and it is very prolific.

*Growth.*—The growth of this rose is very vigorous and quick, and it is especially adapted to greenhouse culture.

*Aroma.*—The redolence of the aroma is very pronounced, being of a delectable tea-fragrance, and its sweet smelling aroma persists until the bloom has withered and is discarded.

*Class.*—This rose is classed as a hybrid tea-rose, and it is of the continuous blooming type.

I claim:

A new variety of hybrid rose, distinguished especially by its bloom presenting a dark yellow color when in bud, changing to an amber yellow color when fully opened, and then changing to a creamy yellow color when fully matured, the soft velvety texture of the petals, the large size of the bloom, its continuous blooming quality, and in the bloom emitting a pronounced aroma of delectable tea-fragrance throughout its entire existence.

ROY L. BYRUM.